US010562872B2

(12) United States Patent
Diness et al.

(10) Patent No.: US 10,562,872 B2
(45) Date of Patent: Feb. 18, 2020

(54) SYNTHESIS OF 1-[2-(2,4-DIMETHYL-PHENYLSULFANYL)-PHENYL]PIPERAZINE

(71) Applicant: H. Lundbeck A/S, Valby (DK)

(72) Inventors: Frederik Diness, Olstykke (DK); Morten Meldal, Copenhagen (DK); Christian Borch Jacobsen, Hillerod (DK)

(73) Assignee: H. Lundbeck A/S, Valby (DK)

(*) Notice: Subject to any disclaimer, the term of this patent is extended or adjusted under 35 U.S.C. 154(b) by 0 days.

(21) Appl. No.: 16/072,596

(22) PCT Filed: Feb. 6, 2017

(86) PCT No.: PCT/DK2017/050026
§ 371 (c)(1),
(2) Date: Jul. 25, 2018

(87) PCT Pub. No.: WO2017/137048
PCT Pub. Date: Aug. 17, 2017

(65) Prior Publication Data
US 2019/0040027 A1 Feb. 7, 2019

(30) Foreign Application Priority Data
Feb. 8, 2016 (DK) .................................. 2016 70066

(51) Int. Cl.
C07D 295/096 (2006.01)
C07D 333/70 (2006.01)
C07D 491/113 (2006.01)
C07D 295/073 (2006.01)
C07C 209/10 (2006.01)
C07D 265/30 (2006.01)
C07D 295/033 (2006.01)
C07D 413/10 (2006.01)
C07C 211/52 (2006.01)

(52) U.S. Cl.
CPC ........ C07D 295/096 (2013.01); C07C 209/10 (2013.01); C07D 265/30 (2013.01); C07D 295/033 (2013.01); C07D 295/073 (2013.01); C07D 333/70 (2013.01); C07D 413/10 (2013.01); C07D 491/113 (2013.01); C07C 211/52 (2013.01)

(58) Field of Classification Search
CPC ............ C07D 295/033; C07D 295/096; C07D 265/30; C07D 413/10; C07D 217/02; C07D 333/70; C07D 491/113; C07D 209/08; C07D 295/073; C07C 211/52; C07C 213/02; C07C 209/10; C07C 217/84; C07B 43/04
See application file for complete search history.

(56) References Cited

U.S. PATENT DOCUMENTS 4,780,667 A 12/1988 Makino et al.
9,353,073 B2 * 5/2016 Ruhland .................. C07F 15/02

FOREIGN PATENT DOCUMENTS

WO   WO 94/03186    2/1994
WO   WO 2010/121621 10/2010
WO   WO2014/191548  12/2014
WO   WO2015/155153  10/2015

OTHER PUBLICATIONS

Parrish, "Synthesis and Characterization of Polymeric Materials Derived from 2,5-Diketopiperazines and Pyroglutamic Acid", https://aquila.usm.edu/theses_dissertations/2382, Jan. 8, 2018.
Supplementary material—list of pharmaceutically acceptable acids, Based on Handbook of Pharmaceutical Salts, excluding polymers, Electronic Supplementary Material for CrystEngComm, This Journal is © The Royal Society of Chemistry 2005.
Parrish et al., "Supramolecular Materials from Multifunctional Pyroglumatic Acid Derivatives", Macromolecules, 36, pp. 4250-4252, 2003.
Smith et al., "Methacrylate Derivatives Incorporating Pyroglutamic Acid", Biomacramolecules, 3, pp. 1392-1399, 2002.
Jarvinen et al., "Enteric Coating Reduces Upper Gastrointestinal Adverse Reactions to Doxycycline", Clin. Drug Invest. 10 (6), pp. 323-327, 1995.
Lu et al., "2,6-Diisopropoxyphenyl(dicyclohexyl)phosphine: A New Ligand for Palladium-Catalyzed Amination Reactions of Aryl Chlorides with Potassium Hydroxide as the Base", Adv. Synt. Cat. 2011 353 100-112.
Guo et al., "Ligand-free iron/copper cocatalyzed N-arylations of aryl halides with amines under microwave irradiation", Green 5 Chem. 2010 12 276-281.
Otsuka et al., "Catalytic SNAr reaction of non-activated fluoroarenes with amines via Ru $n^6$-arene complexes", Chem. Comm. 2010 46 336-338.
Shen et al., "Highly Reactive, General and Long-Lived Catalysts for Palladium-Catalyzed Amination of Heteroaryl and Aryl Chlorides, Bromides, and Iodides: Scope and Structure—Activity Relationships", J. Am. Chem. Soc. 2008 130 6586-6596.
Lerma et al., "Studies on Pd/imidazolium salt protocols for amination of aryl bromides and iodides using lithium hexamethyldisilazide (LHMDS)", Adv. Synt. Cat. 2011 353 100-112.
Urgaonkar et al., "Scope and Limitations of $Pd_2(dba)_3$/P(i-$BuNCH_2CH_2)_3$N-Catalyzed Buchwald-Hartwig Amination Reactions of Aryl Chlorides", J. Org. Chem. 2004 69 9135-9142.
Maes et al., "Rapid palladium-catalyzed amination of aryl chlorides with aliphatic amines under temperature-controlled microwave heating", Tetrahedron 2004 60 11559-11564.
Desmarets et al., "Nickel(0)/Dihydroimidazol-2-ylidene Complex Catalyzed Coupling of Aryl Chlorides and Amines", J. Org. Chem. 2002 67 3029-3036.

(Continued)

Primary Examiner — Alexander R Pagano
Assistant Examiner — Ebenezer O Sackey
(74) Attorney, Agent, or Firm — Fish & Richardson P.C.

(57) ABSTRACT

The invention relates to a method for synthesis of 1-[2-(2,4-Dimethyl-phenylsulfanyl)-phenyl]piperazine in the presence of a strong base.

22 Claims, 1 Drawing Sheet

(56) References Cited

OTHER PUBLICATIONS

Kataoka et al., "Air Stable, Sterically Hindered Ferrocenyl Dialkylphosphines for Palladium-Catalyzed C—C, C—N, and C—O Bond-Forming Cross-Couplings", J. Org. Chem. 2002 67 5553-5566.
Clayden et al, "Organic Chemistry", in Organic Chemistry 2001.
Carey et al., "Part A: Structure and mechanism" http://library.wur.nl/WebQuery/clc/1602925, Advanced Organic Chemistry 2000.
Hansch et al., "A Survey of Hammett Substituent Constants and Resonance and Field Parameters", Chem. Rev. 1991 91 165-195.
International Search Report mailed in corresponding International Application No. PCT/DK2017/050026 (dated Apr. 19, 2017).
Xiangguo, M., et al., "Microwave-Assisted Amination from Fluorobenzenes without Catalyst and Strong Base," Journal of Fluorine Chemistry, vol. 146, Dec. 12, 2012 (Dec. 12, 2012), pp. 70-75.
Jacobsen, et al., "Mechanism and Scope of Base-Controlled Catalyst-Free N-Arylation of Amines with Unactivated Fluorobenzenes," Chemistry—A European Journal, vol. 23, No. 4, Dec. 13, 2016, pp. 846-851.

\* cited by examiner

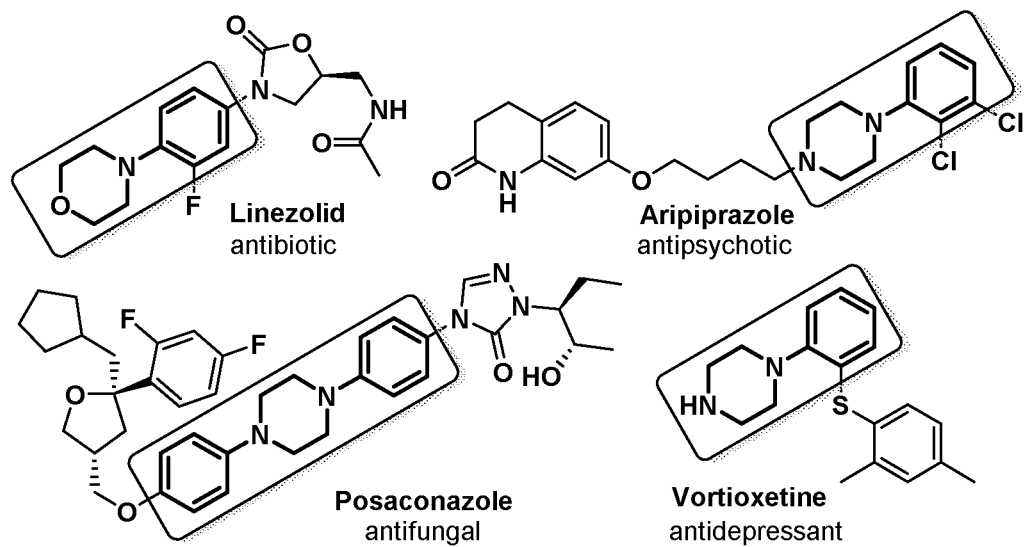

SYNTHESIS OF 1-[2-(2,4-DIMETHYL-PHENYLSULFANYL)-PHENYL]PIPERAZINE

TECHNICAL FIELD

The invention relates to a method for synthesis of 1-[2-(2,4-Dimethyl-phenylsulfanyl)-phenyl]piperazine in the presence of a strong base.

BACKGROUND OF INVENTION

N-arylations of aliphatic amines are important chemical transformations as the resulting aniline derivatives have found broad applications as pharmaceuticals, materials for organic electronics and dyes for industrial and research applications. Pyrazine and morpholine derivatives are of special interest, as these are found in a range of top selling pharmaceuticals.

A range of transition metal-catalyzed reactions has been developed for the formal halide to nitrogen substitution on aryl halides. Most renowned are the Ullmann and Buchwald-Hartwig couplings employing copper and palladium catalysis respectively. These results notwithstanding, the employment of transition metals as catalysts has several drawbacks in industrial applications, especially due to high costs, oxygen sensitivity, challenging purifications and toxic metal contaminants being present in the final products.

To overcome these shortcomings, catalyst-free $S_N Ar$ reactions on highly activated halide-substituted benzene derivatives have been applied. However, the scope of this approach has so far been limited as strongly electron-withdrawing groups, such as nitro or cyano substituents, have been considered essential for reactivity. Thus, leading text books in organic chemistry describes: a) "Without electron-attracting groups present, nucleophilic aromatic substitution occurs only under extreme reaction conditions" F. A. Carey, R. J. Sundberg in Advanced Organic Chemistry: Part A: Structure and Mechanisms; 4th ed. Springer Science and Business Media, New York, 2000. b) "To summarize: Any anion-stabilizing (electron-withdrawing) group ortho or para to a potential leaving group can be used to make nucleophilic aromatic substitution possible." J. Clayden, N. Greeves, S. Warren, P. Wothers in Organic Chemistry; Oxford University Press, New York, 2001.

WO 2014/191548 discloses a synthetic process for the production of 1-(2-((2,4-dimethyl-phenyl)sulfonyl)phenyl) piperazine by arylation in the presence of $Cs_2CO_3$. The process however requires incubation at elevated temperature for more than 14 days.

SUMMARY OF INVENTION

The invention provides methods for preparing 1-[2-(2,4-Dimethyl-phenylsulfanyl)-phenyl]piperazine, said method comprising the steps of
a. Providing piperazine;
b. Providing an electrophile selected from the group consisting of 1, 2-di-fluorobenzene, 2-chloro-fluorobenzene, 1, 2-di-chlorobenzene, 2-(2,4-di-methyl-thiophenol-yl)-chlorobenzene, and 2-(2,4-di-methyl-thiophenol-yl)-fluorobenzene;
c. Providing a base having a pKa above 32 in DMSO and/or a pKa above 26 in THF;
d. Providing an organic solvent that only contain protons with a pKa above 32 in DMSO,
e. Reacting said piperazine with said electrophile in said organic solvent in the presence of the base and in the absence of a transition metal catalyst, there by obtaining
   i. 1-[2-fluoro-phenyl]piperazine or 1-[2-chloro-phenyl]piperazine; or
   ii. 1-[2-(2,4-dimethyl-phenylsulfanyl)-phenyl]piperazine.
f. If obtaining 1-[2-fluoro-phenyl]piperazine or 1-[2-chloro-phenyl]piperazine in step e. reacting said 1-[2-fluoro-phenyl]piperazine or 1-[2-chloro-phenyl]piperazine with 1-sulfanyl-2,4-dimethyl-benzene, thereby obtaining 1-[2-(2,4-Dimethyl-phenylsulfanyl)-phenyl] piperazine
g. Optionally purifying the 1-[2-(2,4-dimethyl-phenylsulfanyl)-phenyl]piperazine.

DESCRIPTION OF DRAWINGS

FIG. 1: Examples of pharmaceuticals containing an N-arylated secondary amine.

DETAILED DESCRIPTION OF THE INVENTION

Definitions

The term "alkane" refers to saturated linear or branched carbohydrides of the general formula $C_n H_{2n+2}$.

The term "alkenyl" as used herein refers to a substituent derived from an alkene by removal of one —H. An alkene may be any acyclic carbonhydride comprising at least one double bond. Frequently, alkenyl will have the general formula —$C_n H_{2n-1}$.

The term "alkyl" refers to a substituent derived from an alkane by removal of one —H.

The term "alkynyl" as used herein refers to a substituent derived from an alkyne by removal of one —H. An alkyne may be any acyclic carbonhydride comprising at least one triple bond. Frequently, alkynyl will have the general formula —$C_n H_{2n-3}$.

The term "amino" as used herein refers to a substituent of the general formula

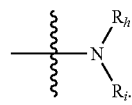

The waved line indicates the point of attachment of the substituent. Amino may thus for example be —$NH_2$ or —NH—.

The term "arene" as used herein refers to aromatic mono- or polycyclic carbonhydrides.

The term "aromatic" refers to a chemical substituent characterised by the following:
- contains a delocalized conjugated π system, most commonly an arrangement of alternating single and double bonds
- has a coplanar structure, with all the contributing atoms in the same plan
- the contributing atoms are arranged in one or more rings
- it contains a number of π delocalized electrons that is even, but not a multiple of 4.

The term "aromatic carbon atom" as used herein refers to a carbon atom, which contributes to an aromatic moiety.

Consequently a "non-aromatic carbon atom" is a carbon atom which is not an integral part of an aromatic moiety. Accordingly, a non-aromatic carbon atom may optionally be linked to an aromatic moiety by a covalent bond. By way of examples, all carbon atoms of a phenyl group are considered "aromatic carbon atoms", however the carbon atoms of an alkyl group covalently linked to phenyl are considered "non-aromatic carbon atoms".

The term "aryl" as used herein refers to a substituent derived from an arene by removal of one —H from a C in the ring. Examples of useful aryls to be used with the present invention comprise phenyl, napthyl, anthracenyl, phenanthrenyl, and pyrenyl.

The term halogen as used herein refers to a substituent selected from the group consisting of —F, —Cl, —Br and —I.

The term "heteroaryl" as used herein refers to a substituent derived from an heteroarene by removal of one —H from an atom in the ring structure of said heteroarene. Heteroarenes are mono- or polycyclic aromatic compounds comprising one or more heteroatoms in the ring structure. Said heteroatoms are preferably selected from the group consisting of S, N and O. Non limiting examples of useful heteroaryls to be used with the present invention comprise azolyl, pyridinyl, pyrimidinyl, furanyl, and thiophenyl.

The term "non-aromatic heterocycle" refers to a mono- or polycyclic compound, which is not aromatic, and which comprises one or more heteroatom in the ring structure. Said heteroatoms are preferably selected from the group consisting of S, N and O. Examples of non-aromatic heterocycle includes but are not limited to pyrrolidine, piperidine, piperazine, morpholine, and thiomorpholine.

The term "phosphinyl" as used herein refers to a substituent of the general structure

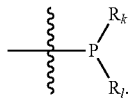

The waved line indicates the point of attachment of the substituent. Thus, phosphinyl may be —PH$_3$.

The term pKa as used herein refers to the negative logarithmic of the dissociation constant $K_a$ for an acid in a given solvent: $pK_a = -\text{Log}_{10} K_a$.

$K_a$, also called the acidity constant, is defined as:

$$K_a = \frac{[A^-][SH^+]}{[HA][S]}$$

for the reaction:

$$HA + S \rightleftharpoons A^- + SH^+$$

wherein S is the solvent and HA is an acid that dissociates into A-, known as the conjugate base of the acid, and a hydrogen ion which combines with a solvent molecule. When the concentration of solvent molecules can be taken to be constant, $K_a$, is:

$$K_a = \frac{[A^-][H^+]}{[HA]}$$

The term "substituted" as used herein in relation to chemical compounds refers to hydrogen group(s) being substituted with another moiety. Thus, "substituted with X" as used herein in relation to chemical compounds refers to hydrogen group(s) being substituted with X. Similarly, "substituted X" refers to X, wherein one hydrogen group has been substituted with another moiety. By way of example "substituted alkyl" refers to alkyl-R, wherein R is any moiety but —H.

The term "substituent" as used herein in relation to chemical compounds refers to an atom or group of atoms substituted in place of a hydrogen atom.

The term "strongly electron withdrawing substituents" as used herein refers to substituents with a Hammet meta substituent constant above 0.5, as described in Hanhsch 1991, and/or substituents having a double bond to oxygen of the linking atom.

The term "thioalkyl" as used herein refers to a substituent of the general formula —S— alkyl.

The term "thioaryl" as used herein refers to a substituent of the general formula —S-aryl.

The term "transition metal catalyst" refers to a compound capable of catalysing a chemical reaction, wherein said compound comprises a transition element or an ion of a transition element. A transition element is an element whose atom has an incomplete d sub-shell, or which can give rise to cations with an incomplete d sub-shell.

Method for Preparing an Arylated Amine

The present invention provides methods for preparing 1-[2-(2,4-Dimethyl-phenylsulfanyl)-phenyl]piperazine. In particular, the methods of the present invention can be performed even in the absence of a transition metal catalyst.

In one embodiment the invention relates to methods for preparing 1-[2-(2,4-Dimethyl-phenylsulfanyl)-phenyl]piperazine, said methods comprising the steps of a. Providing piperazine;
b. Providing an electrophile selected from the group consisting of 1, 2-di-fluorobenzene, 2-chloro-fluorobenzene, 1, 2-di-chlorobenzene, 2-(2,4-di-methyl-thiophenol-yl)-chlorobenzene and 2-(2,4-di-methyl-thiophenol-yl)-fluorobenzene;
c. Providing a base, which for example may be any of the bases described herein below in the section "Base";
d. Providing an organic solvent, which for example may be any of the solvents described herein below in the section "Solvent"
e. reacting said piperazine with said electrophile in said organic solvent in the presence of the base and in the absence of a transition metal catalyst, there by obtaining
    i. 1-[2-fluoro-phenyl]piperazine, or 1-[2-chloro-phenyl]piperazine; or
    ii. 1-[2-(2,4-dimethyl-phenylsulfanyl)-phenyl]piperazine,
f. If obtaining 1-[2-fluoro-phenyl]piperazine or 1-[2-chloro-phenyl]piperazine in step e. reacting said 1-[2-fluoro-phenyl]piperazine or 1-[2-chloro-phenyl]piperazine with 1, sulfanyl-2,4-dimethyl-benzene, thereby obtaining 1-[2-(2,4-dimethyl-phenylsulfanyl)-phenyl]piperazine
g. Optionally purifying the 1-[2-(2,4-dimethyl-phenylsulfanyl)-phenyl]piperazine, wherein steps a., b., c. and d. may be performed in any order.

The steps a., b., c. and d. may be performed in any suitable order. In one embodiment step e) comprises the sub-steps of
i) Reacting said nucleophile with said base,
ii) Reacting the product of sub-step i) with said electrophile,
wherein sub-steps i) and ii) are performed in the indicated order. This may in particular be the case in embodiments of the invention, where a strong base is used, e.g. a base, wherein the corresponding acid has a pKa above 45, such as above 49.

Said 2-(2,4-di-methyl-thiophenol-yl)-chlorobenzene or 2-(2,4-di-methyl-thiophenol-yl)-fluorobenzene may have been obtained by a cross coupling reaction. For example, said 2-(2,4-di-methyl-thiophenol-yl)-chlorobenzene or 2-(2, 4-di-methyl-thiophenol-yl)-fluorobenzene may have been obtained by reacting
i. 1, 2-di-fluorobenzene, 2-chloro-fluorobenzene, or 1, 2-di-chlorobenzene with
ii. 2,4-dimethyl-phenylsulfanyl.

Said reaction may be performed in the presence of a base and an organic solvent. Said base may be a milder base, than the base used in the N-arylation reactions of the invention.

As mentioned above one advantage of the methods according to the present invention is that the methods can be performed in the absence of a transition metal catalyst. Thus, it is preferred that step e. is performed in the absence of a transition metal catalyst. In some embodiments, it may be preferred that the methods are performed in the absence of any transition metals, and in particular that step e. is performed in the absence of any transition metals. In particular, it may be preferred that the methods are performed in the absence of cupper, palladium and nickel, and in particular that step e. is performed in the absence of any cupper, palladium and nickel. Thus, the reaction, and in particular step e. is preferably performed in the absence of cupper, palladium and nickel in any oxidation state and any form.

Reacting said nucleophile with said electrophile may be done at any useful temperature. Thus, step e. may be performed at any useful temperature. One advantage of the methods of the invention is that the methods generally can be performed at temperatures, which are easy to handle, even in large scare. Thus, reacting said nucleophile with said electrophile may be performed at a temperature of at the most 120° C., such as at the most 110° C. Frequently even lower temperatures can be applied.

Reacting said nucleophile with said electrophile may be done for a time sufficient to allow the reaction. Thus, step e. may be performed for sufficient time to allow the reaction. One advantage of the methods of the invention is that generally a relative short time is required for the reactions. Thus, said nucleophile may typically be allowed to react with said electrophile for at the most one week. Frequently, the reaction may be even faster, thus in some embodiments of the invention, said nucleophile may be allowed to react with said electrophile for at the most 900 min, such as for at the most 720 min, such as for the most 180 min, for example for in the range of 5 to 900 min or 5 to 720.

Nucleophile and Electrophile

Piperazine act as nucleophile in the current methods for preparing 1-[2-(2,4-Dimethyl-phenylsulfanyl)-phenyl]piperazine. Piperazine may be in the form of a salt with various inorganic or organic acids. In embodiments of the invention, where 1-[2-(2,4-Dimethyl-phenylsulfanyl)-phenyl]piperazine is for pharmaceutical use, said salt may be a pharmaceutically acceptable salt.

In one embodiment, the electrophile is selected from the group consisting of 1, 2-di-fluorobenzene, 2-chloro-fluorobenzene, 1, 2-di-chlorobenzene, 2-(4,2-di-methyl-thiophenol-yl)-fluorobenzene, and 2-(4,2-di-methyl-thiophenol-yl)-chlorobenzene.

The electrophile may be a product of an organic synthesis and may thus be considered an intermediate. For example, the electrophile may be a product of a cross coupling reaction.

Base

The methods of the present invention involve reacting a nucleophile and an electrophile in the presence of a base. Preferably said base is a base, wherein the corresponding acid has a pKa above 29, such as at least 30 in DMSO. It may also be preferred that said base has a pKa above 25, preferably at least 26 in THF. Thus, it is generally preferred that the base is not a weak base, for example the base is preferably not $Cs_2CO_3$.

In some embodiments of the invention the base may be a base, wherein the corresponding acid has a pKa above 32 in DMSO. In some embodiments the base may be a base, wherein the corresponding acid has a pKa above 26 in THF.

In some embodiments of the invention it may be preferred that the base is not too strong. Thus, in some embodiments it is preferred that the base is a base, wherein the corresponding acid has a pKa in the range of 29 to 49, such as in the range of 29 to 45. In other embodiments the base is a base, wherein the corresponding acid has a pKa in the range of 32 to 49, such as in the range of 32 to 45. Aforementioned pKa is preferably determined in DMSO.

pKa may be determined by any conventional method. pKa values in DMSO is preferably measured up to the value of 35, and values above 35 may be extrapolated as described in Bordwell, Acc. Chem. Res. 1988, 21, 456-463.

The corresponding acid to butyllithium (BuLi) has a pKa 50, and may thus in some embodiments be less preferable. Thus, in some embodiments the base is a base, wherein the corresponding acid has a pKa above 29, for example above 32, with the proviso that the base is not BuLi.

In one embodiment the base is selected from the group consisting of lithium bis(trimethylsilyl)amide (LiHMDS), sodium bis(trimethylsilyl)amide (NaHMDS), potassium bis(trimethylsilyl)amide (KHMDS), lithium 2,2,6,6,-tertmethylpiperidide (LiTMP), and BuLi.

In some embodiments, the base is a metal hydride, such as an alkali metal hydride. In some embodiments, the base is selected from the group consisting of lithium hydride, sodium hydride, potassium hydride, cesium hydride, magnesium hydride, calcium hydride, lithium aluminium hydride, sodium aluminium hydride, potassium aluminium hydride, lithium borohydride, sodium borohydride and potassium borohydride.

In some embodiments, the base is a non-nucleophilic base, i.e. a base only acting as a nucleophile in the removal of protons. Typical non-nucleophilic bases are sterically hindered and bulky, preventing them from attacking as nucleophiles. Hence, protons can attach to the basic center of the base but alkylation and complexation is inhibited. Examples of non-nucleophilic bases are lithium diisopropylamide (LDA), LiTMP and silicon-based amides such as LiHMDS, NaHMDS and KHMDS. Generally, non-nucleophilic bases are sterically hindered and bulky, and thus the base may be a base having a Mw of at least 120, preferably of at least 130, such as of at least 140. More preferably the base has aforementioned Mw and aforementioned pKa. Thus, it may be preferred that the base has:
a pKa above 29 in DMSO and/or a pKa in THF above 25; and
a Mw of at least 120 or a Mw of at least 140.

In other embodiments the base is selected from the group consisting of LiHMDS, NaHMDS, KHMDS and LiTMP.

Solvent

The methods of the present invention involve reacting a nucleophile and an electrophile in a solvent and in the presence of a base. The solvent may be any organic solvent.

In one embodiment the solvent may be chosen according to the base used in the particular reaction. Thus, the solvent may be an organic solvent, which is stable in the presence the base employed under the reaction conditions employed.

In addition, it is preferred that the solvent is a liquid at the reaction temperature.

It is preferred that the solvent is a solvent that only contain protons with a pKa above 35.1 in DMSO. In one embodiment the solvent is a solvent that only contains protons with a pKa above 32 in DMSO. In one embodiment the solvent is not DMSO. Thus, the solvent may be a solvent that only contains protons with a pKa above 32 in DMSO, with the proviso that the solvent is not DMSO.

In one embodiment the solvent is a solvent that does not contain any carbonyl groups. In one embodiment the solvent is a solvent that does not contain any sulfoxide groups. The solvent may for example be selected from the group consisting of ethers, alkanes, benzene and substituted benzene.

Ethers useful as solvent include any ether. In particular, the ether may be an ether, which only contain protons with a pKa above 32, for example above 35.1 in DMSO. It may further be preferred that the ether is a liquid at the reaction temperature. It may further be preferred that the ether does not contain any carbonyl groups. The ether may for example be selected from the group consisting of tetrahydrofuran (THF), dioxane, dimethoxyethane (DME), 2-methyl-tetra-hydrofuran (2-Me-THF), and diethoxyethane.

Alkanes useful as solvent include any alkane. In particular, the alkane may be an alkane, which only contain protons with a pKa above 32, for example above 35.1 in DMSO. It may further be preferred that the alkane is a liquid at the reaction temperature. It may further be preferred that the alkane does not contain any carbonyl groups. The alkane may be a linear, branched or cyclic alkane, e.g. a $C_{4-20}$ linear, branched or cyclic alkane. For example, the alkane may be methylcyclohexane.

Substituted benzenes useful as solvent include any substituted benzene. In particular, the substituted benzene may be a substituted benzene, which only contain protons with a pKa above 32, for example above 35.1 in DMSO. It may further be preferred that the substituted benzene is a liquid at the reaction temperature. It may further be preferred that the substituted benzene does not contain any carbonyl group. The substituted benzene is in general different from the electrophile used in the reaction. However in some embodiments, the electrophile may also be used as solvent. For example the substituted benzene may be substituted with one or more substituents selected from the group consisting of $C_{1-3}$-alkyl. In addition or alternatively, the benzene may be substituted with up to 1 —Cl. The substituted benzene may for example be selected from the group consisting of toluene, xylene and chlorobenzene.

EXAMPLES

The invention is further illustrated by the following examples, which however should not be construed as being limiting for the invention.

Example 1

N-arylation of compound 1a (N-methylpiperazine) with compound 2 (1,3,5-trifluorobenzene) was performed using the following general reaction conditions: 1a (0.2 mmol) and the base (0.5 mmol) was mixed in solvent (0.5 mL) at room temperature. Different solvents, bases and temperatures were tested.

After 10 minutes 2 (0.6 mmol) was added and reaction heated to temperature and stirred for 12 h. Yields assessed by HPLC. The results are shown in table 1 below.

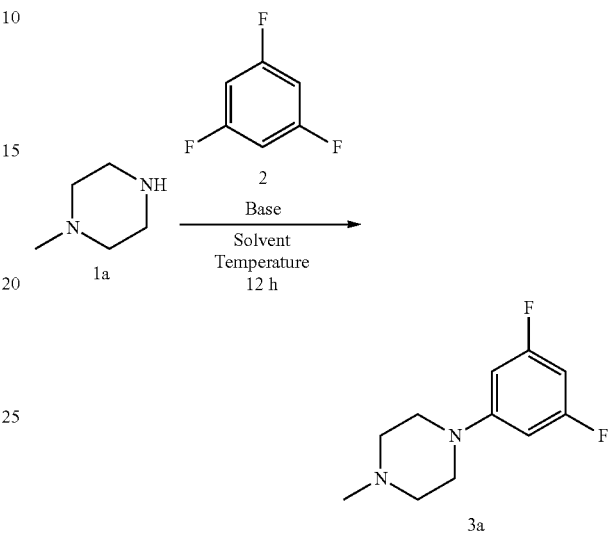

TABLE 1

| Entry | Base | $M_w$ (g/mol) | $pK_a$ DMSO | $pK_a$ THF | Solvent | Temperature | Yield 3a (%)[a] |
|---|---|---|---|---|---|---|---|
| A | None | — | — | — | THF | 50° C. | 0 |
| B | $Cs_2CO_3$ | 325.82 | ** | ** | THF | 50° C. | 0 |
| C | LiO$^t$Bu | 80.05 | 29 | | THF | 50° C. | <5 |
| D | LiHMDS | 167.33 | 30*** | 26 | THF | 50° C. | >95 |
| E* | LiTMP | 147.19 | 37 | | THF | 90° C. | 42 (3b) |
| F | LiHMDS | 167.33 | 30*** | 26 | DME | 50° C. | 73 |
| G | LiHMDS | 167.33 | 30*** | 26 | 2-Me-THF | 50° C. | 51 |

[a]Evaluated by HPLC.
*1-fluoro-3-methoxybenzene used instead of 1,3,5-trifluorobenzene.
** pKa of $Cs_2CO_3$ is expected to be lower than 29 in DMSO and 25 in THF.
***pKa of LiHMDS has been reported to be 30 in DMSO (http://www.d-bernier.fr/pKa.php)

The reaction was successfully performed using LiOtBu as base, but it was significantly less efficient than using some of the other bases.

Example 2

A two steps reaction applying first a weaker nucleophile followed by an amine nucleophile proved viable in the synthesis of recently marketed pharmaceutical antidepressant Vortioxetine 9 (scheme 1). Applying thiophenol as the weaker nucleophile followed by addition of piperazine. proved highly applicable in this approach, illustrated by the synthesis of recently marketed pharmaceutical antidepressant Vortioxetine 9 from 1,2-difluorobenzene. This should be compared to the present industrial production process, which utilizes two subsequent cross-coupling reactions on 2-bromo-iodobenzene.

Scheme 1: Preparation of Vortioxetine. DMA = dimethylacetamide.

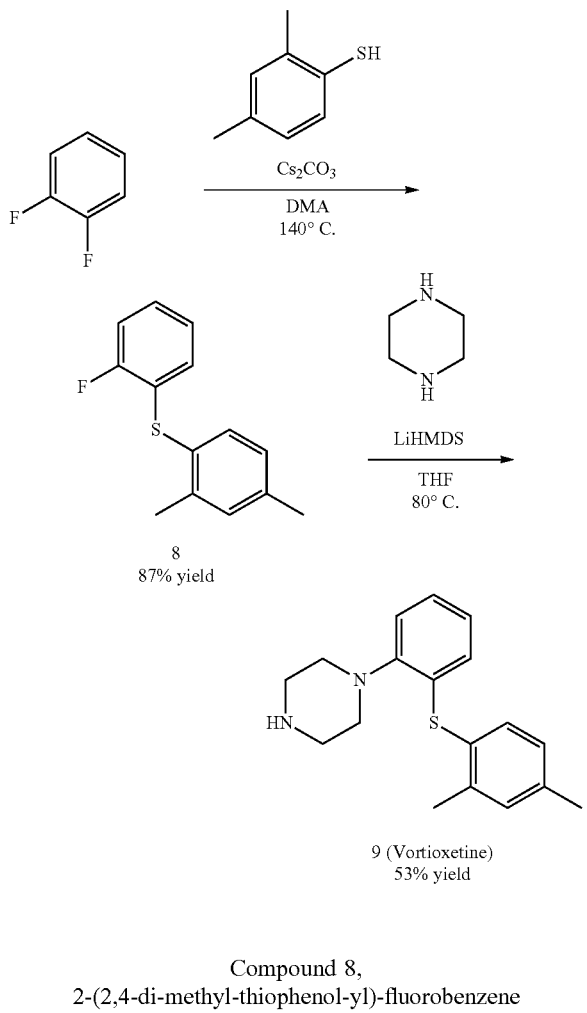

Compound 8,
2-(2,4-di-methyl-thiophenol-yl)-fluorobenzene

To a vial was added 2,4-dimethylthiophenol (1.0 mmol), 1,2-difluorobenzene (2.0 mmol), Cs$_2$CO$_3$ (2.5 mmol) and dimethylacetamide (2.0 mL). The vial was sealed and stirred at 140° C. for 4 hours. The reaction was quenched with water and brine and then extracted into Et$_2$O. After evaporation, the product 8 was purified by chromatographyon silica gel, and isolated in 87% yield as a clear oil. $^1$H NMR (CDC$_3$) δ ppm 7.28 (d, J=7.8 Hz, 1H), 7.19-7.09 (m, 2H), 7.09-7.03 (m, 1H), 7.02-6.95 (m, 2H), 6.87 (td, J=7.7, 1.7 Hz, 1H), 2.37 (s, 3H), 2.34 (s, 3H). $^{13}$C NMR (CDCl$_3$) δ ppm 160.0 (d, J=245.2 Hz), 141.0, 138.9, 134.4, 131.7, 130.2 (d, J=1.9 Hz), 127.7, 127.6, 127.5 (d, J=7.5 Hz), 124.6 (d, J=3.5 Hz), 124.4, 115.5 (d, J=21.8 Hz), 21.1, 20.5.

Compound 9, 1-[2-(2,4-Dimethyl-phenylsulfanyl)-phenyl]piperazine

Piperazine (1.25 mmol), 2-(2,4-di-methyl-thiophenol-yl)-fluorobenzene (8) (0.25 mmol) and LiHMDS (1.0 M in THF, 1.0 mmol) were mixed and heated in a sealed vial. After 2 hours at 80° C. the reaction was quenched by the addition of HCl (0.01M in H$_2$O), the solvent evaporated and the compound redissolved in CH$_3$CN:H$_2$O (1:1). The compound 9 was isolated as the HCl salt by chromatography on C18 gel (0 to 50% CH$_3$CN in 0.01 M HCl) in 53% yield as white solid. $^1$H NMR (DMSO-d$_6$) δ ppm 9.41 (s, 2H), 7.33 (d, J=7.8 Hz, 1H), 7.24 (d, J=1.9 Hz, 1H), 7.16-7.07 (m, 3H), 6.96 (ddd, J=7.9, 5.9, 2.7 Hz, 1H), 6.44-6.39 (m, 1H), 3.21 (s, 8H), 2.32 (s, 3H), 2.24 (s, 3H). $^{13}$C NMR (DMSO-d$_6$) δ 147.8, 141.6, 139.3, 135.7, 133.3, 131.7, 128.1, 126.8, 126.0, 125.8, 125.1, 120.2, 48.1, 43.3, 20.7, 20.1.

The invention provides a novel method for the amination of unactivated halobenzene derivatives. A key factor for reactivity is the applied base's ability to sufficiently deprotonate the amine nucleophile under the applied reaction conditions without simultaneously degrading the halobenzene electrophile. For secondary aliphatic amines the reactions proceed readily by addition of a simple base such as LiHMDS, and thus circumvent the need for transition metals. The reactions proceed with great regio- and chemoselectivity.

REFERENCES

Hansch et al. Chem. Rev. 1991, 91, 165-195
C. Desmarets, R. Schneider, Y. Fort, J. Org. Chem. 2002, 67, 3029-3036
N. Kataoka, Q. Shelby, J. P. Stambuli, J. F. Hartwig, J. Org. Chem. 2002, 67, 5553-5566
B. U. Maes, K. T. Loones, S. Hostyn, G. Diels, G. Rombouts, Tetrahedron 2004, 60, 11559-11564
S. Urgaonkar, J. G. Verkade, J. Org. Chem. 2004, 69, 9135-9142
I. C. Lerma, M. J. Cawley, F. G. Cloke, K. Arentsen, J. S. Scott, S. E. Pearson, J. Hayler, S. Caddick, J. Organomet. Chem. 2005, 690, 5841-5848
Q. Shen, T. Ogata, J. F. Hartwig, J. Am. Chem. Soc. 2008, 130, 6586-6596
M. Otsuka, K. Endo, T. Shibata, Chem. Comm. 2010, 46, 336-338
D. Guo, H. Huang, Y. Zhou, J. Xu, H. Jiang, K. Chen, H. Liu, Green Chem. 2010, 12, 276-281
B. Lü, P. Li, C. Fu, L. Xue, Z. Lin, S. Ma, Adv. Synt. Cat. 2011, 353, 100-112.
Jacobsen, C. B.; Meldal, M.; Diness, F. Chemistry—A European Journal, 2016, accepted, DOI: 10.1002/chem.201604098

The invention claimed is:

1. A method for preparing 1-[2-(2,4-Dimethyl-phenylsulfanyl)-phenyl]piperazine, said method comprising the steps of
reacting a piperazine with an electrophile in an organic solvent in the presence of a base and in the absence of a transition metal catalyst, thereby obtaining
i. 1-[2-fluoro-phenyl]piperazine or 1-[2-chloro-phenyl]piperazine; or
ii. 1-[2-(2,4-dimethyl-phenylsulfanyl)-phenyl]piperazine,
wherein the electrophile is selected from the group consisting of 1, 2-di-fluorobenzene, 2-chloro-fluorobenzene, 1, 2-di-chlorobenzene, 2-(2,4-di-methyl-thiophenol-yl)-chlorobenzene, and 2-(2,4-di-methyl-thiophenol-yl)-fluorobenzene; the base has a pKa above 29 in DMSO or a pKa above 25 in THF; and the organic solvent only contains protons with a pKa above 32 in DMSO;
if 1-[2-fluoro-phenyl]piperazine or 1-[2-chloro-phenyl]piperazine is obtained, reacting said 1-[2-fluoro-phenyl]piperazine or 1-[2-chloro-phenyl]piperazine with 1-sulfanyl-2,4-dimethyl-benzene, thereby obtaining 1-[2-(2,4-Dimethyl-phenylsulfanyl)-phenyl]piperazine; and
optionally purifying the 1-[2-(2,4-dimethyl-phenylsulfanyl)-phenyl]piperazine.

2. The method according to claim 1, wherein 2-(2,4-di-methyl-thiophenol-yl)-chlorobenzene or 2-(2,4-di-methyl-thiophenol-yl)-fluorobenzene has been obtained by reacting
   i. 1, 2-di-fluorobenzene, 2-chloro-fluorobenzene, or 1, 2-di-chlorobenzene with
   ii. 2,4-dimethyl-phenylsulfanyl.

3. The method according to claim 1, wherein reacting the piperazine with the electrophile comprises the sub-steps of i) reacting the piperazine with said base and ii) reacting the product of step i) with said electrophile, and wherein sub-steps i) and ii) are performed in the indicated order.

4. The method according to claim 1, wherein the solvent only contains protons with a pKa above 35.1 in DMSO.

5. The method according to claim 1, wherein the solvent contains no carbonyl groups.

6. The method according to claim 1, wherein the solvent contains no sulfoxide groups.

7. The method according to claim 1, wherein the solvent is selected from the group consisting of ethers, alkanes, benzene and substituted benzene.

8. The method according to claim 7, wherein the ether is selected from the group consisting of tetrahydrofuran (THF), dioxane, dimethoxyethane (DME), and 2-methyl-tetrahydrofuran (2-Me-THF).

9. The method according to claim 7, wherein the alkane is a liquid at the reaction temperature.

10. The method according to claim 7, wherein the alkane is methylcyclohexane.

11. The method according to claim 7, wherein the substituted benzene is benzene substituted with one or more substituents selected from the group consisting of C1-3-alkyl and —Cl, wherein said benzene is substituted with at most 1 —Cl.

12. The method according to claim 7, wherein the substituted benzene is selected from the group consisting of xylene, toluene and chlorobenzene.

13. The method according to claim 1, wherein the base has a corresponding acid that has a pKa of less than 45 in THF.

14. The method according to claim 1, wherein the base is selected from the group consisting of LiHMDS, NaHMDS, KHMDS, LiTMP, and BuLi.

15. The method according to claim 1, wherein the base is selected from the group consisting of LiHMDS, NaHMDS, KHMDS and LiTMP.

16. The method according to claim 1, wherein reacting the piperazine with the electrophile is performed at a temperature of at most 120° C.

17. The method according to claim 1, wherein reacting the piperazine with the electrophile takes places for at most one week.

18. The method according to claim 1, wherein reacting the piperazine with the electrophile takes places for 5 to 900 minutes.

19. The method according to claim 1, wherein said 1-[2-(2,4-dimethyl-phenylsulfanyl)-phenyl]piperazine is obtained as a salt thereof.

20. The method of claim 1, wherein reacting the piperazine with the electrophile is performed at a temperature of at most 110° C.

21. The method of claim 1, wherein reacting the piperazine with the electrophile takes places for 5 to 720 minutes.

22. The method of claim 1, wherein the solvent is selected from the group consisting of tetrahydrofuran (THF), dioxane, dimethoxyethane (DME), and 2-methyl-tetrahydrofuran (2-Me-THF), and the base is selected from the group consisting of LiHMDS, NaHMDS, KHMDS and LiTMP.

* * * * *